(12) United States Patent
Melcher et al.

(10) Patent No.: US 9,255,890 B2
(45) Date of Patent: Feb. 9, 2016

(54) APPARATUS FOR MEASURING THE SCATTERED LIGHT AND METHOD OF TESTING A RECEPTION OPTICS

(71) Applicant: SICK Engineering GmbH, Ottendorf-Okrilla (DE)

(72) Inventors: Uwe Melcher, Ottendorf-Okrilla (DE); Jürgen Regehr, Ottendorf-Okrilla (DE)

(73) Assignee: SICK ENGINEERING GMBH, Ottendorf-Okrilla (DE)

( * ) Notice: Subject to any disclaimer, the term of this patent is extended or adjusted under 35 U.S.C. 154(b) by 0 days.

(21) Appl. No.: 14/511,456

(22) Filed: Oct. 10, 2014

(65) Prior Publication Data
US 2015/0103345 A1    Apr. 16, 2015

(30) Foreign Application Priority Data
Oct. 11, 2013   (DE) .......................... 10 2013 111 256

(51) Int. Cl.
| | |
|---|---|
| G01N 21/00 | (2006.01) |
| G01N 21/94 | (2006.01) |
| G01N 21/15 | (2006.01) |
| G01N 21/51 | (2006.01) |
| G01N 21/53 | (2006.01) |
| G01N 21/47 | (2006.01) |

(52) U.S. Cl.
CPC ............... *G01N 21/94* (2013.01); *G01N 21/15* (2013.01); *G01N 21/47* (2013.01); *G01N 21/51* (2013.01); *G01N 21/53* (2013.01); *G01N 2021/157* (2013.01); *G01N 2201/06113* (2013.01)

(58) Field of Classification Search
USPC .................................................. 356/337–343
See application file for complete search history.

(56) References Cited

U.S. PATENT DOCUMENTS 6,449,042 B1 * 9/2002 Hamann ............ G01N 15/0211
356/339

FOREIGN PATENT DOCUMENTS

| DE | 60222043 T2 | 6/2008 |
|---|---|---|
| EP | 1881319 A1 | 1/2008 |
| EP | 1881319 B1 | 1/2008 |
| GB | 2412166 A | 9/2005 |

OTHER PUBLICATIONS

Examination Report issued in German Application No. 10 2013 11 256.0 dated Sep. 5, 2014, (5) pages.

* cited by examiner

*Primary Examiner* — Tri T Ton
(74) *Attorney, Agent, or Firm* — Nath, Goldberg & Meyer; Jerald L. Meyer; Christopher Thomas

(57) ABSTRACT

An apparatus for measuring light scatter, the apparatus having a light transmitter and reception optics for transmitting and detecting a light beam scattered in a measured zone, respectively, wherein an adjustment unit changes between a measuring mode wherein the optical axes of the light transmitter and the reception optics stand at an angle with respect to one another and intersect in the measured zone and a test mode wherein the optical axes of the light transmitter and the reception optics are parallel, wherein the light beam successively sweeps over the reception optics. The reception optics is rotatably held at a displaceable rotary axle, wherein the adjustment unit first rotates the reception optics about the rotary axle in the test mode until the optical axis of the reception optics is parallel with the optical axis of the light transmitter and then displaces the rotatable axle together with the reception optics.

14 Claims, 1 Drawing Sheet

APPARATUS FOR MEASURING THE SCATTERED LIGHT AND METHOD OF TESTING A RECEPTION OPTICS

FIELD OF THE INVENTION

The invention relates to an apparatus for measuring the light scattered from a measured zone and to a method of testing a reception optics of such an apparatus in accordance with the preamble of claims 1 and 11 respectively.

BACKGROUND

A measurement volume is irradiated by means of a light source in the scattered light measurement. If scatter centers, for example dust grains or other particles, are located in the measurement volume, the light is scattered. A light receiver set up at an angle to the irradiated light registers this scattered light which allows conclusions on the kind and quantity of the particles in the measurement volume. The scattered light measurement is used, for example, in environmental metrology or in emission technology.

Over the course of time, the measurement precision can be impaired by contamination or by other effects. To compensate this, a self-test function is known which is actually prescribed with proof-tested emission measurement devices. A possibility of a self-test comprises testing the optical boundary surface of the light receiver with the light source. For this purpose, the light receiver is moved from its measurement position into a test position in which the light is received in a direct line of sight without scattering in the measurement volume. An expected reception intensity in the test position corresponds to the maximum signal so that a representative transmission measurement of the optical boundary surface is made possible. If the reception optics is contaminated, the expected signal is correspondingly attenuated, from which a conclusion can be drawn on a contamination and its degree.

The prior art is familiar with different constructions with which the light receiver can be moved into the beam of the light source. In the simplest case, the light transmitter and the light receiver are pivoted with respect to one another until they are in a direct line of sight. To avoid an overmodulation, an attenuation filter can be arranged in the line of sight. If impairments of the reception optics are to be detected in a spatially resolved manner, a relative movement during the self-test is provided so that the light beam scans the reception optics bit by bit. The light detector can be pivoted on a circular path, for example. However, this has the disadvantage that the light is incident at different angles during the self-test and thus falsifies the result.

A further conventional sliding mechanism arranges the light receiver at the free end of a leaf spring. The leaf spring is bent by a slider for the self-test until the light receiver is in the line of sight of the light transmitter. Small movements of the plate spring are then sufficient to achieve the desired scanning. The light receiver also moves on a circular path with this design. In addition, the plate spring can suffer fatigue from the changing mechanical strains and can break in the worst case.

It is known from EP 1 881 319 B1 to check a reception optics of an apparatus for measuring the light scatter in that the reception optics is guided by a positive cam. This positive cam has two sections, with the reception optics being swept over on the first section by the transmitted light beam on a movement and a test thus being made while the second section provides that the reception optics is moved into the initial test position. This design solves the problem, but it cannot be used for all scattered light measurement devices from a construction aspect.

Overall, the known mechanisms have admittedly proved themselves in some applications, but do not always satisfy the demands on precision, take up too much construction space or are not suitable for all applications from a construction aspect for other reasons.

SUMMARY OF THE INVENTION

It is therefore the object of the inventing to provide an alternative for carrying out a self-test.

This object is satisfied by an apparatus for measuring the light scattered from a measured zone and by a method of testing a reception optics of such an apparatus in accordance with claims 1 and 11 respectively. A change is made between a measurement mode and a test mode for a scattered light measurement. In the measurement mode, the optical axes of the light transmitter and of the reception optics stand at an angle with respect to one another, in particular at an acute angle, so that there is no direct line of sight from the light transmitter to the light receiver. In this manner, light is registered which is scattered by a medium to be tested such as an aerosol in the measured zone or measurement volume. In the test mode, the reception optics is tested for contaminants or other impairments. In this respect, the invention starts from the basic idea of holding the reception optics rotatably at a displaceable rotary axle. This allows the reception optics first to be pivoted about the rotary axle until its optical axis is in parallel with the optical axis of the light transmitter. The rotary axle is subsequently displaced, which results in a parallel displacement of the optical axis of the reception optics which can in this manner be scanned bit by bit with a direct line of sight to the light transmitter.

The invention has the advantage that a mechanical design has been found which satisfies set conditions on size, shape and arrangement of the components such as a predefined housing or a specific positioning and alignment of the optical components. In this respect, a high stability and service life of the mechanical adjustment is achieved with a simultaneously favorable manufacture and simple assembly, putting into operation and adjustment.

The reception optics is preferably fastened to a first holding element which is rotatably held at the displaceable rotary axle. The reception optics itself frequently does not offer any mechanical point of engagement for the rotary axle so that it is instead fixed to the first holding element. The reception optics thereby follows rotations and displacements of the first holding element directly.

The scattered light measurement apparatus preferably has a rotationally fixed second holding element from which the rotary axle starts. The rotary axle thus connects the second holding element and the first holding element or reception optics respectively. In this respect, the second holding element forms the rotationally fixedly stationary counter piece with respect to which the reception optics is pivoted about the rotary axle.

The second holding element is preferably displaceably supported, in particular on at least one rail or linear guide. The possible direction of displacement has at least one component perpendicular to the optical axis of the light transmitter. This serves to move the rotary axle and thus the reception optics during the scanning by the light beam in the test mode.

A first restoring element is preferably provided to push the reception optics back into a starting position on the change from the test mode into the measuring mode. The first restoring element, for example, has a spring which is stretched during the displacement of the rotary axle and subsequently pulls it back into a position of rest. The first restoring element is preferably fastened to the second holding element and to a fixed point, for instant a housing.

The adjustment unit preferably has a pushing element which can be displaced in a straight line from a first position into a second position. The straight-line displacement of the pushing element is transferred into the two-part pivot and translation movement. The pushing element engages at the reception optics or at the first holding element at a point offset from the rotary axle. Initially, the reception optics evades by pivoting. When the optical axes of the reception optics and the light transmitter are in parallel, the pivot movement ends and the pushing element effects the parallel displacement of the reception optics to scan it.

A chamfered surface of the pushing element is preferably in contact with the reception optics or with the first holding element. The chamfered surface forms the region of engagement with which the reception optics is pivoted and then displaced. The reception optics or the first holding element respectively preferably have a corresponding sloped surface which contacts the chamfered surface of the pushing element.

A first abutment is preferably provided, in particular on the second holding element, to end the rotational movement when the optical axis of the reception optics is in parallel with the optical axis of the light transmitter. The first abutment therefore prevents a rotational movement beyond the desired parallel test position with a direct line of sight. As soon as the end of the rotational movement has been reached, the first abutment forces the evasion of a further effect by the adjustment unit, in particular of a pushing element with a sloped engagement surface differently than by continuing the rotational movement, namely by a displacement used for the scanning of the reception optics.

A second restoring element is preferably provided to rotate the reception optics back into a starting position on the change from the test mode into the measuring mode. If therefore the displacement unit or a pushing element respectively has the load removed, the reception optics rotates back into its measurement position in which it stands at an angle to the light beam. The second restoring element can be a spring which is, for example, fastened between the reception optics or the first holding element and the second holding element respectively.

A second abutment is preferably provided, in particular on the second holding element, to rotate the reception optics at most back up to and into the starting position. It is thereby prevented on a change from the test mode into the measurement mode that a rotation back beyond the desired scatter angle takes place.

The method in accordance with the invention can be further developed in a similar manner and shows similar advantages in so doing. Such advantageous features are described in an exemplary, but not exclusive manner in the subordinate claims dependent on the independent claims.

BRIEF DESCRIPTION OF THE DRAWINGS

The invention will be explained in more detail in the following also with respect to further features and advantages by way of example with reference to embodiments and to the enclosed drawing. The Figures of the drawing show in.

DETAILED DESCRIPTION

Figure 1:
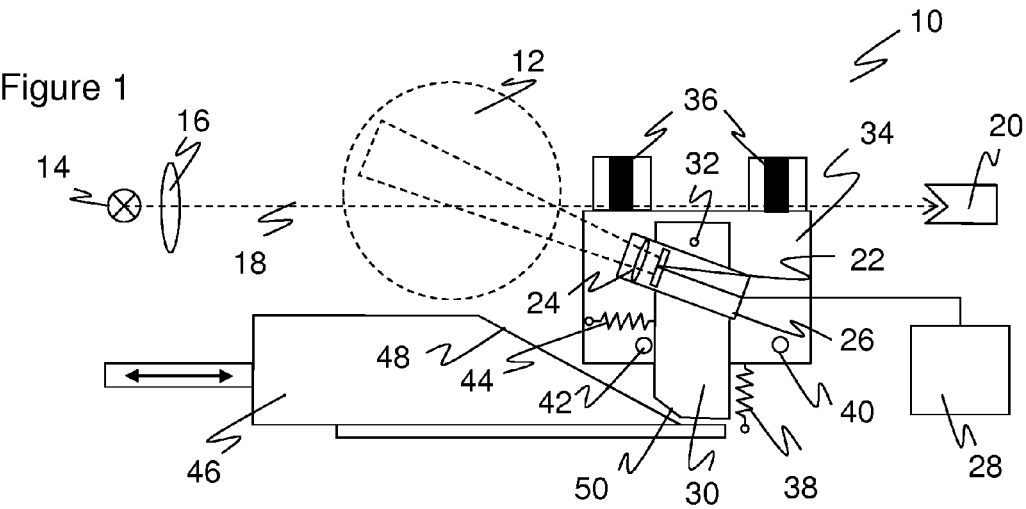
FIG. 1 a schematic representation of an apparatus for the measurement of the light scattered in a measurement mode.

FIG. 1 shows a schematic representation of a light scatter measurement apparatus 10 in a measurement mode. A medium, for example a gas or a liquid, is located in a measured zone or measurement volume 12 which is marked by a dashed circle. The measurement volume 12 is open in the illustration, but can also be bounded by a measurement cell having corresponding windows for the light passage, with this also being necessary at least in the case of a liquid as the medium.

A light transmitter 14 having an associated transmission optics 16 transmits a light beam 18 into the measurement volume 12. The light transmitter 14 preferably comprises a laser light source to be able to generate a tightly focused high-intensity light beam 18 Portions of the light beam 18 which transmit the measurement volume 12 without hindrance are absorbed in a light trap 20 on an oppositely disposed side or are reflected away there. If scatter centers, for example dust or other particles, are located in the measurement volume 12, at least a portion of the light beam 18 is scattered out of the direct line of sight to the light trap 20.

A light receiver 22 having an upstream reception optics 24 is directed to the measurement volume 12. Strictly speaking, the effective measurement volume 12 is determined exactly as the intersection zone of the light beam 18 and the reception aperture. The light receiver 22 with its reception optics 24 can be accommodated in a housing 26. To determine the scattered light portions, the optical axis of the light receiver 22 or of its reception optics 24 stands at an acute angle of, for example, 15° with respect to the optical axis of the light transmitter 14. Light is thus received in a corresponding forward scattering. A corresponding obtuse angle would alternatively have to be selected for the measurement of backscatter, i.e. the light receiver 22 is then seated on the other side of the measurement volume 12 next to the light transmitter 14. The light receiver 22 is, for example, a photodiode having a preferably large dynamic extent in order to be able to detect both scattered light and the direct light beam 18.

An evaluation unit 28 is connected to the light receiver 22 to draw conclusions on the medium in the measurement volume 12 from its received signal and in particular from the intensity of the scattered light. A visual range can thus be determined, for example, a fire can be recognized by means of smoke development or the degree of pollution of air with harmful substances can be recognized.

FIG. 1 shows the light scatter measurement apparatus 10 in the measurement mode in which the light receiver is arranged at a scatter angle to the measurement volume 12 to be measured. For the selective transition into a test mode in which the reception optics 24 is checked for contaminants and other impairments, an adjustment mechanism is provided which will be described in more detail in the following. In this respect, checking the reception optics 24 also always means that a transparent boundary surface, for instance a window of the housing 26, closing to the outside is checked. The reception optics 24 can, however, differing from the illustration, also itself form the outer transition of the housing 26.

The mechanical arrangement comprises a first holding element 30 to which the reception optics 24 or its housing 26 is rotationally fixedly and positionally fixedly attached. Every movement of the first holding element 30 is therefore directly transferred to the reception optics 24. The first holding element 30 is held at a rotary axle 32 for example a pin, a spigot or a rod, and can thus be pivoted or rotated about the rotary axle.

The rotary axle 32 is fixed at a second holding element 34 which is itself rotationally fixed with respect to the scattered light measurement apparatus 10. The second holding element 34 is in turn supported on rails 36 and can thus be displaced in a direction perpendicular to the optical axis of the light transmitter 14 and thus to the light beam 18. A first spring 38 is, on the one hand, fastened to the second holding element 34 and, on the other hand, is fixed in the scattered light measurement apparatus 10. A displacement of the second holding element 34 thus takes place against the spring force of the first spring 38 and, when relieved, the first spring 38 pulls the second holding element 34 back into a starting position. In a corresponding position, this could also take place by its own weight.

Furthermore, a first abutment 40 and a second abutment 42 are located on the second holding element 34 and bound the possible rotational movement of the first holding element 30 with respect to both sides. A second spring 44 is fastened to the first holding element 30 and to the second holding element 34 so that the rotational movement of the first holding element 30 about the rotary axle 32 takes place against the spring force of the second spring 44. If no other force is acting on the first holding element 30, the second spring 44 pulls the first holding device 30 back into a starting position of the rotational movement.

A pushing element 46 is provided to be traveled in a straight line between a first position and a second position. The displacement preferably takes place in parallel with the optical axis of the light transmitter 14; an oblique positioning with respect to it would, however, be possible. A chamfered surface 48 of the pushing element 46 contacts the first holding element 30. The first holding element also has a chamfer 50 in the region of the contact surface. The movement of the pushing element 46 is effected by a drive, not shown, which is, for example, addressed by the evaluation unit 28.

Figure 2:
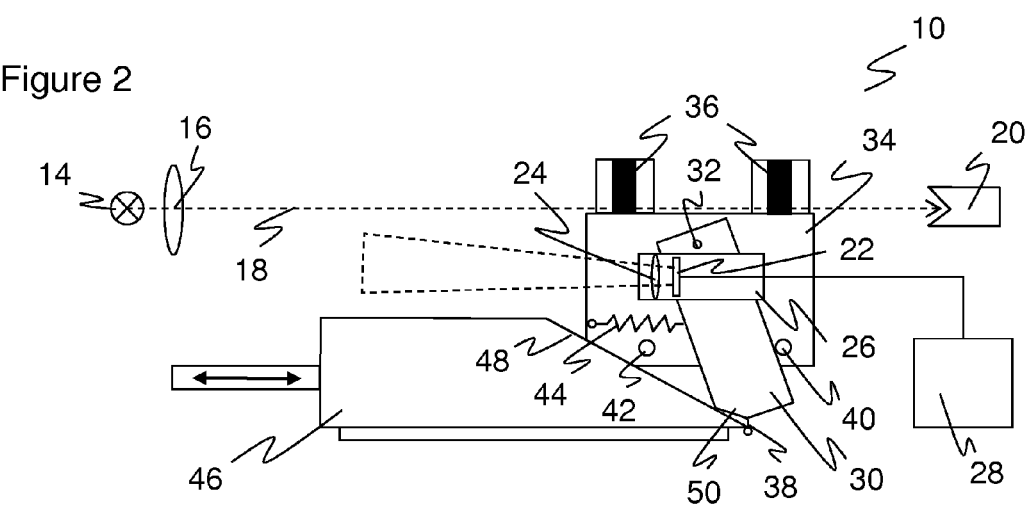
FIG. 2 a schematic representation of the apparatus in accordance with FIG. 1 on the change into a test mode after conclusion of a rotational movement and at the start of a subsequent displacement.
Figure 3:
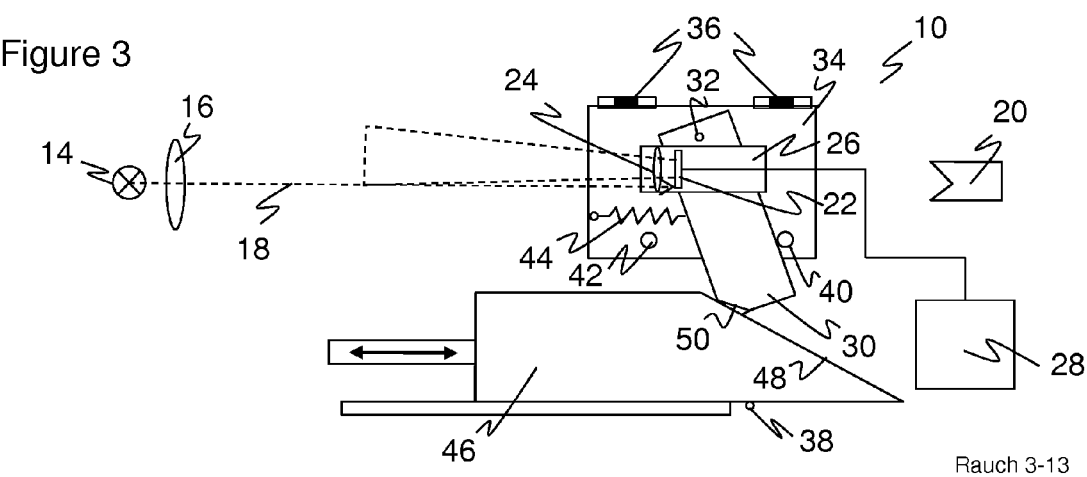
FIG. 3 a schematic representation of the apparatus in accordance with FIG. 1 after completion of the displacement started in a position in accordance with FIG. 2.

The interaction of these just-described elements of the adjustment mechanism is illustrated by FIGS. 2 and 3. The test mode has two phases, with the reception optics 24 being rotated in the first phase so that the optical axis of the reception optics initially standing at the scatter angle with respect to the light beam 18 is aligned in parallel and thus in a direct line of sight to the light transmitter 14.

The end of this first phase is shown in FIG. 2. The pushing element is displaced from the first position of the measurement mode in accordance with FIG. 1 into an intermediate position. In this respect, the pushing element 46 takes along the first holding element 30 by the contact between the chamfered surface 48 with the first holding element 30. The first holding element 30 evades in that it rotates about the rotary axle 32, and indeed for so long until the abutment 40 blocks a further rotation.

In a second phase, the reception optics 24 is then displaced in parallel so that the light beam 18 is moved over the reception optics 34 while maintaining a direct line of sight between the light transmitter 14 and the light receiver 22 and scans it for contaminants or other impairments with spatial resolution.

FIG. 3 shows the scattered light measurement apparatus 10 at the end or just before the end of the second phase. The pushing element 46 is displaced out of the intermediate position in accordance with FIG. 2 further in the direction of the second position reached in FIG. 3. The first holding element 30 can no longer evade the pushing element 46 by a rotational movement due to the abutment 40.

Instead, the chamfered surface 48 provides that the second holding element 34 is moved on the rails 36. The region of the displacement of the second holding element 34 should preferably start, irrespective of possible differences in the illustration, just so that the light beam 18 is incident on a lower end region of the reception optics 24 in the intermediate position of the pushing element 46 and is incident on an upper end region of the reception optics 24 in the second position of the pushing element 46. The reception optics 24 is then completely swept over by the light beam 18 just once.

The evaluation unit 28 has an expectation which is predefined ex works or which is taught as to which intensity should be measured for an error-free operation and can therefore recognize deviations in the test mode and initiate required measures such as a service demand or a dynamic adaptation of transmission power or reception sensitivity. The scattered light measurement apparatus 10 thus tests itself for errors due to contamination, damage or another impairment of the reception optics 24 by a cyclic change into the test position. In this respect, impairments of the transmission optics 16 are preferably also recognized at the same time.

If the pushing element 45 is moved back into the first position again after the end of a test to change back from the test mode into the measurement mode, the first spring 38 first retracts the second holding element 34 on the rails 36 into its starting position. A further scanning of the reception optics 24 can take place during this process. Subsequently, the second spring 44 also contracts and in so doing rotates the first holding element 30 about the rotary axle 32 until the first holding element 30 cannot further follow the second spring 44 due to the second abutment 42 and the reception optics has thus again reached the starting position of the measurement mode.

The invention claimed is:

1. An apparatus (10) for measuring the light scattered from a measured zone (12), the apparatus having a light transmitter (14) for transmitting a light beam (18) into the measured zone (12) and having a light receiver (22) with a reception optics (24) for detecting light scattered in the measured zone (12), wherein an adjustment unit is provided to change between a measuring mode in which the optical axes of the light transmitter (14) and of the reception optics (24) stand at an angle with respect to one another and intersect in the measured zone (12) and a test mode in which the optical axes of the light transmitter (14) and of the reception optics (24) are aligned in parallel with one another, wherein the light beam (18) successively sweeps over the reception optics (24) for recognizing contaminants, and wherein the reception optics (24) is rotatably held at a displaceable rotary axle (32); and the adjustment unit first rotates the reception optics (24) about the rotary axle until the optical axis of the reception optics (24) is in parallel with the optical axis of the light transmitter (14) in the test mode and then displaces the rotary axle (32) together with the reception optics (24).

2. An apparatus (10) in accordance with claim 1,
wherein the reception optics (24) is fastened to a first holding element (30) which is rotatably held at the displaceable rotary axle (32).

3. An apparatus (10) in accordance with claim 1,
the apparatus having a rotationally fixed second holding element (34) from which the rotary axle (32) starts.

4. An apparatus (10) in accordance with claim 3, wherein the second holding element (34) is displaceably supported, in particular on at least one rail (36) or linear guide.

5. An apparatus (10) in accordance with claim 1, wherein a first restoring element (38) is provided to push the reception optics (24) back into a starting position on the change from the test mode into the measuring mode.

6. An apparatus (10) in accordance with claim 1, wherein the adjustment unit has a pushing element (46) which is displaceable in a straight line from a first position into a second position.

7. An apparatus (10) in accordance with claim 6, wherein a chamfered surface (48) of the pushing element (46) is in contact with the reception optics (24) or with the first holding element (30).

8. An apparatus (10) in accordance with claim 1, wherein a first abutment (40) is provided to end the rotational movement when the optical axis of the reception optics (24) is in parallel with the optical axis of the light transmitter (14).

9. An apparatus (10) in accordance with claim 1, the apparatus having a rotationally fixed second holding element (34) from which the rotary axle (32) starts, wherein a first abutment (40) is provided to end the rotational movement when the optical axis of the reception optics (24) is in parallel with the optical axis of the light transmitter (14).

10. An apparatus (10) in accordance claim 1, wherein a second restoring element (44) is provided to rotate the reception optics (24) back into a starting position on the change from the test mode into the measuring mode.

11. An apparatus (10) in accordance with claim 1, wherein a second abutment (42) is provided, to rotate the reception optics (24) back at most up to and into the starting position.

12. An apparatus (10) in accordance with claim 1, the apparatus having a rotationally fixed second holding element (34) from which the rotary axle (32) starts and wherein a second abutment (40) is provided at the second holding element to end the rotational movement when the optical axis of the reception optics (24) is in parallel with the optical axis of the light transmitter (14).

13. A method of testing a reception optics (24) of an apparatus for measuring the light scattered in a measured zone, the apparatus having a light transmitter (14) for transmitting a light beam (18) into the measured zone (12) and having a light receiver (22) with a reception optics (24) for detecting light scattered in the measured zone (12), wherein an adjustment unit is provided to change between a measuring mode in which the optical axes of the light transmitter (14) and of the reception optics (24) stand at an angle with respect to one another and intersect in the measured zone (12) and a test mode in which the optical axes of the light transmitter (14) and of the reception optics (24) are aligned in parallel with one another, wherein the reception optics (24) is scanned by a light beam (18) in a test mode in that the optical axis of the reception optics (24) is tilted until it is in parallel with the light beam (18) and is subsequently displaced in parallel, wherein the reception optics (24) is first tilted about a rotary axle (32) and the rotary axle (32) is subsequently displaced together with the reception optics (24).

14. An apparatus (10) for measuring the light scattered from a measured zone (12), the apparatus having a light transmitter (14) for transmitting a light beam (18) into the measured zone (12) and having a light receiver (22) with a reception optics (24) for detecting light scattered in the measured zone (12), wherein an adjustment unit is provided to change between a measuring mode in which the optical axes of the light transmitter (14) and of the reception optics (24) stand at an angle with respect to one another and intersect in the measured zone (12) and a test mode in which the optical axes of the light transmitter (14) and of the reception optics (24) are aligned in parallel with one another, wherein the light beam (18) successively sweeps over the reception optics (24) for recognizing contaminants, wherein the reception optics (24) is fastened to a first holding element (30) which is rotatably held at a displaceable rotary axle (32), wherein the adjustment unit has a pushing element (46) which is displaceable in a straight line from a first position through an intermediate position into a second position and comprises a chamfered surface (48) which is in contact with the first holding element (30); and the adjustment unit first rotates the reception optics (24) about the rotary axle by moving the pushing element (46) from the first position into the intermediate position taking along the first holding element (30) by the contact between the chamfered surface (48) with the first holding element (30) until the optical axis of the reception optics (24) is in parallel with the optical axis of the light transmitter (14) in the test mode and then displaces the rotary axle (32) together with the reception optics (24) by moving the pushing element (46) from the intermediate position into the second position so that the light beam (18) is moved over the reception optics (24).

* * * * *